US012638373B2

(12) United States Patent
Bessemer et al.

(10) Patent No.: US 12,638,373 B2
(45) Date of Patent: May 26, 2026

(54) SYSTEMS AND METHODS FOR DETECTING AEROSOLIZED VIRAL PARTICLES

(71) Applicant: Opteev Technologies, Inc., Baltimore, MD (US)

(72) Inventors: Conrad Bessemer, Millersville, MD (US); Susan Bessemer, Millersville, MD (US); Biplab Pal, Ellicot City, MD (US)

(73) Assignee: Opteev Technologies, Inc., Baltimore, MD (US)

( * ) Notice: Subject to any disclaimer, the term of this patent is extended or adjusted under 35 U.S.C. 154(b) by 159 days.

(21) Appl. No.: 18/149,637

(22) Filed: Jan. 3, 2023

(65) Prior Publication Data

US 2023/0213429 A1 Jul. 6, 2023

Related U.S. Application Data

(60) Provisional application No. 63/296,037, filed on Jan. 3, 2022.

(51) Int. Cl.
| | |
|---|---|
| *G01N 1/22* | (2006.01) |
| *G01N 15/06* | (2006.01) |
| *G01N 33/00* | (2006.01) |

(52) U.S. Cl.
CPC ....... *G01N 15/0656* (2013.01); *G01N 1/2202* (2013.01); *G01N 33/0027* (2013.01); *G01N 2001/2223* (2013.01)

(58) Field of Classification Search
CPC ............. G01N 15/0656; G01N 1/2202; G01N 33/0027; G01N 2001/2223; G01N 2015/0046; G01N 33/0031; G01N 33/0036; G01N 33/0047; G01N 33/0057

USPC ...... 435/5, 29, 30, 34, 235.1, 287.1; 429/90, 429/92, 93; 436/43, 46, 52, 147; 438/90; 73/23.34, 31.01, 31.02, 31.05, 31.06, 73/864.81; 422/93, 98
See application file for complete search history.

(56) References Cited

U.S. PATENT DOCUMENTS

| | | | |
|---|---|---|---|
| 4,288,544 | A | 9/1981 | Suzuki et al. |
| 8,859,297 | B2 | 10/2014 | Alocilja et al. |
| 9,424,734 | B1 | 8/2016 | Hagi et al. |
| 10,327,692 | B2 | 6/2019 | Uchiyama |
| 2003/0186351 | A1 | 10/2003 | Machida et al. |
| 2004/0239344 | A1 | 12/2004 | Hu |
| 2005/0003396 | A1 | 1/2005 | Ozkan et al. |
| 2012/0085927 | A1 | 4/2012 | Maeng et al. |

(Continued)

FOREIGN PATENT DOCUMENTS

| | | |
|---|---|---|
| EP | 2459984 B1 | 6/2018 |
| IN | 2020-21002188 | 7/2021 |

(Continued)

OTHER PUBLICATIONS

ISR and Written Opinion of PCT/US0222/014873 dated May 23, 2022.

(Continued)

*Primary Examiner* — Robert R Raevis
(74) *Attorney, Agent, or Firm* — Fox Rothschild LLP

(57) ABSTRACT

Systems and methods are provided for reliably detecting aerosolized virus particles using electrochemical characteristics of the virus, and its interaction with π-conjugated conducting solid-state substrates.

13 Claims, 3 Drawing Sheets

Divided air sampler to have a pointed viral drop and co-located voltage pickup

(56) References Cited

U.S. PATENT DOCUMENTS

| | | | |
|---|---|---|---|
| 2012/0225423 A1 | 9/2012 | Schwoebel et al. | |
| 2012/0252003 A1 | 10/2012 | Schmera et al. | |
| 2013/0158378 A1* | 6/2013 | Berger | A61B 5/14546 |
| | | | 438/49 |
| 2015/0355133 A1 | 12/2015 | Prasad | |
| 2016/0025677 A1 | 1/2016 | Chung et al. | |
| 2017/0227486 A1 | 8/2017 | Bhansali et al. | |
| 2019/0232282 A1 | 8/2019 | Pierson et al. | |
| 2019/0250153 A1 | 8/2019 | Muthukumar et al. | |
| 2020/0240939 A1 | 7/2020 | Prasad et al. | |
| 2021/0239635 A1 | 8/2021 | Prasad et al. | |
| 2021/0293706 A1* | 9/2021 | Tropp | G01N 21/645 |
| 2021/0386317 A1 | 12/2021 | Prasad et al. | |
| 2022/0018797 A1 | 1/2022 | Botte et al. | |

FOREIGN PATENT DOCUMENTS

| | | | |
|---|---|---|---|
| KR | 10-2017-0096092 A | 8/2017 | |
| KR | 10-1934946 B1 | 1/2019 | |
| WO | WO 2005-031300 A2 | 4/2005 | |
| WO | WO 2007-104058 A2 | 9/2007 | |
| WO | WO 2012/047865 A2 | 4/2012 | |
| WO | WO-2017085939 A1 * | 5/2017 | .......... G01N 27/126 |
| WO | WO 2019-142599 A1 | 7/2019 | |

OTHER PUBLICATIONS

ISR and Written Opinion of PCT/US2021/061129 dated Mar. 18, 2022.

ISR and Written Opinion of PCT/US2021/048296 dated Dec. 21, 2021.

Alkhouri, et al., "Analysis of breath volatile organic compounds as a noninvasive tool to diagnose nonalcoholic fatty liver disease in children," European journal of gastroenterology & hepatology, vol. 26, No. 1, pp. 82-87, 2014.

Alkhouri, et al.; "Isoprene in the Exhaled Breath is a Novel Biomarker for Advanced Fibrosis in Patients with Chronic Liver Disease: A Pilot Study Clinical and Translational Gastroenterology" 6(9):p. e112, Sep. 2015. | DOI: 10.1038/ctg.2015.40.

* cited by examiner

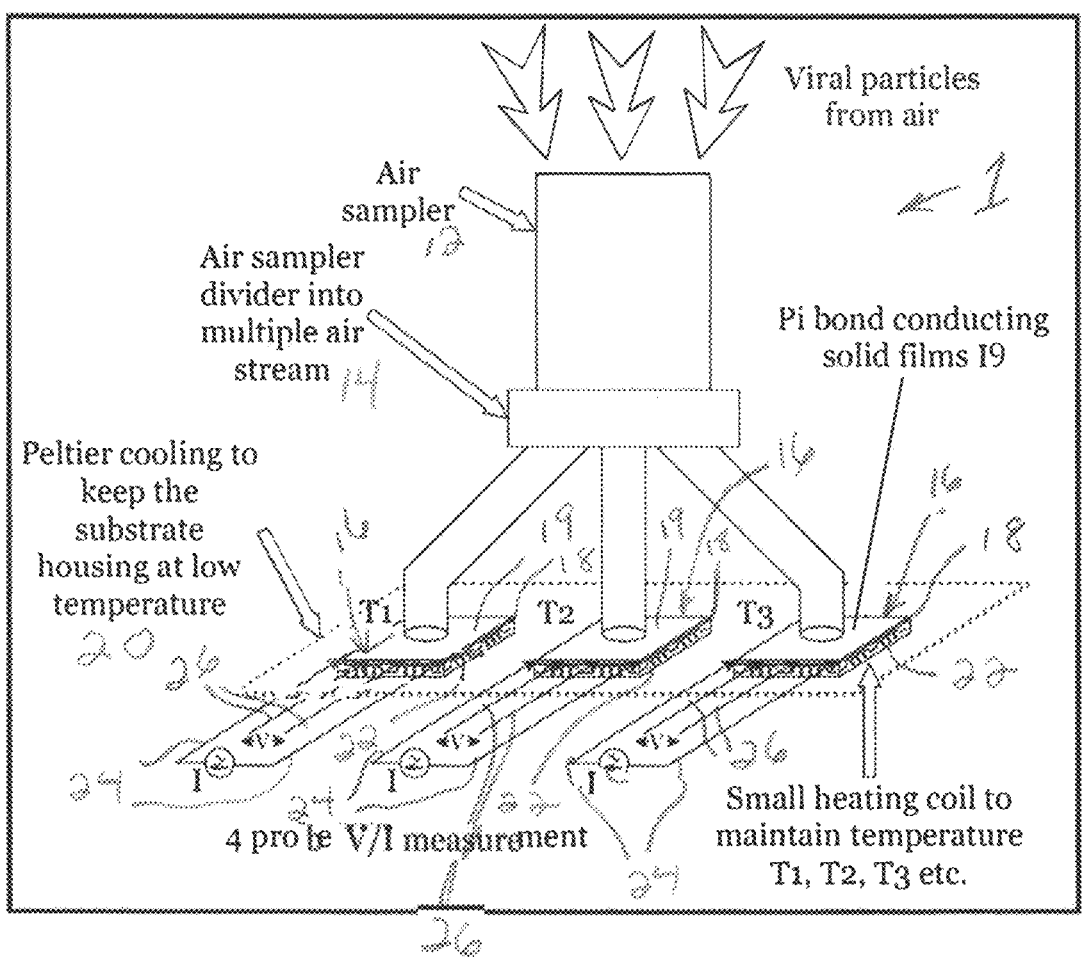
Fig. 1: Divided air sampler to have a pointed viral drop and co-located voltage pickup

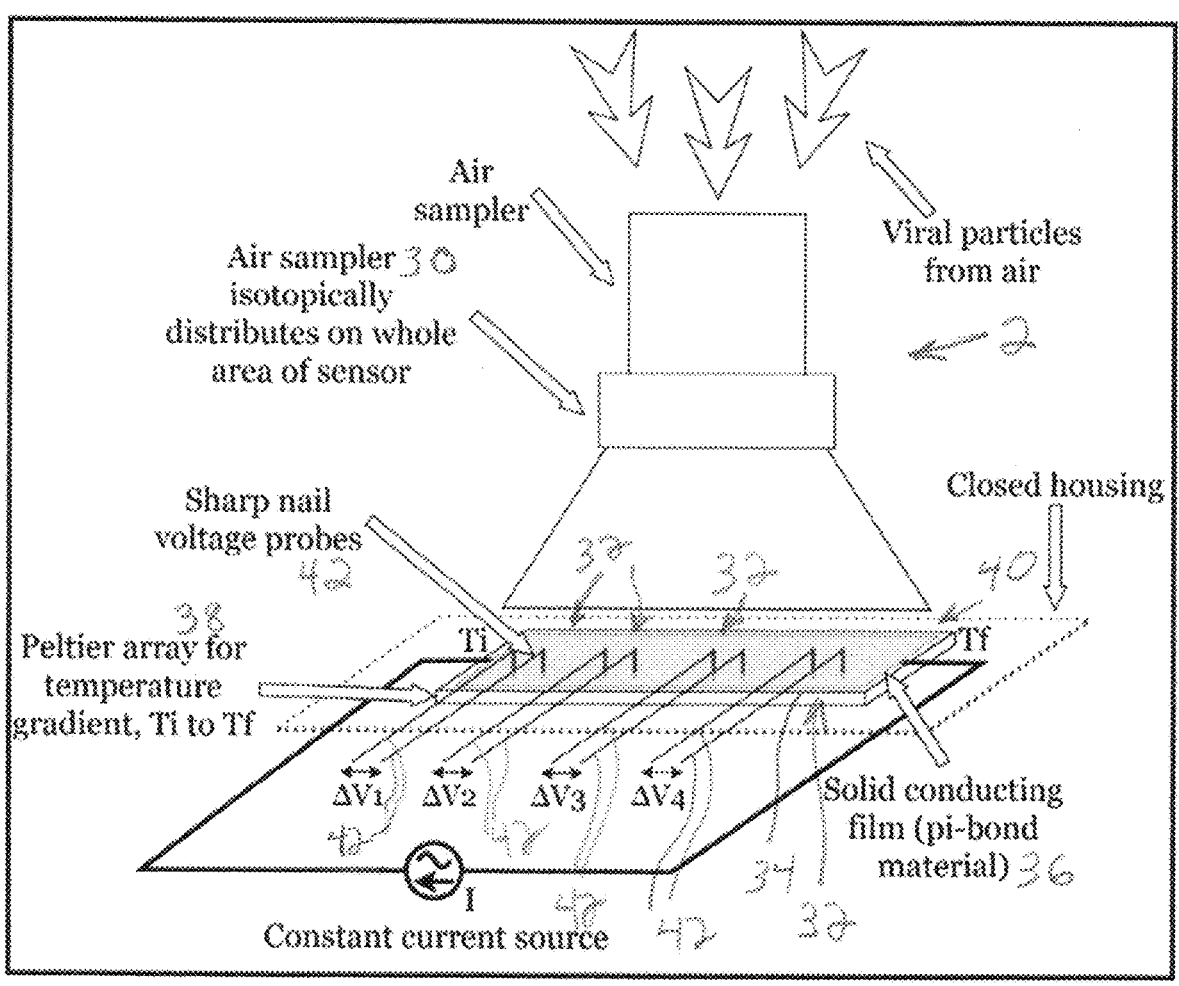
Fig-2: Multiple voltage drop pick up and a single strip application

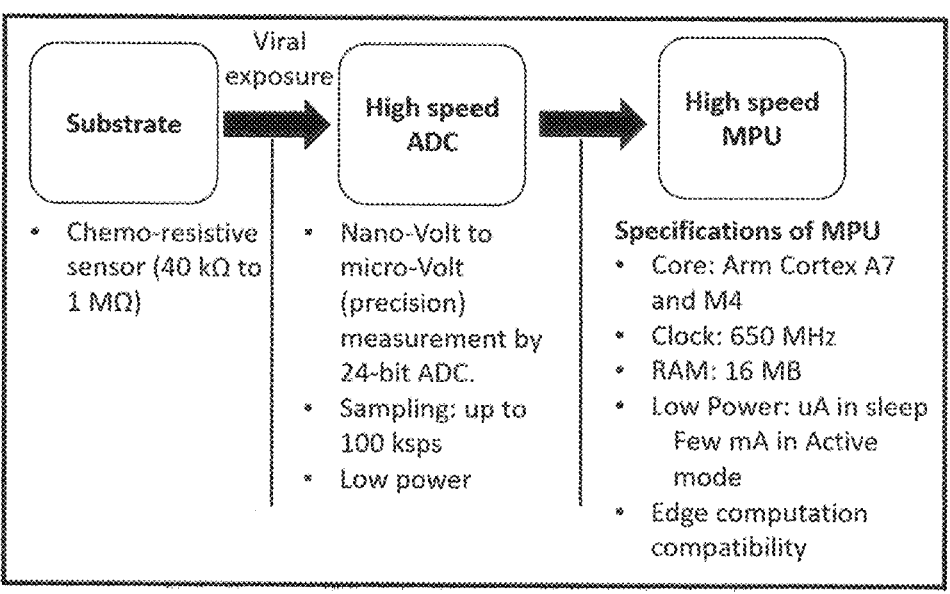
Fig. 3: Electronic schematic for capturing the analog voltage data

SYSTEMS AND METHODS FOR DETECTING AEROSOLIZED VIRAL PARTICLES

BACKGROUND

Rapid, accurate, portable, and large-scale diagnostic technologies for the detection of severe acute respiratory syndrome-coronavirus-2 (SARS-CoV-2) are crucial for controlling the spread of coronavirus disease 2019 (COVID-19). Moreover, air-transmissible diseases involving viruses, such as influenza and coronaviruses, are responsible for a broad range of adverse health effects, and the risk of exposure to such airborne viruses has increased nowadays owing to the utilization of enclosed spaces in many buildings. Several solutions have been introduced to attempt to solve the above problems. There are few relevant disclosures available in the prior-art, which have been identified herein for reference. There are several approaches for the detection of virus particles targeting unique electrochemistry of viral particles (see Detection of Covid 19: A review of the current literature and future perspectives. PMCID: PMC 7371595, and Ultrasensitive Detection of Pathogenic Viruses with electrochemical biosensors: state of the art. PMCID:PMC 7363606), and solid-state materials coated with π-conjugated conducting polymers like Polyaniline, Polypyrrole, etc. (see Method for detection and differentiation of Bacteria and Viruses in Samples, Indian Patent Application 202021002188), or graphene-like π-conjugated materials (see Human Virus detection by Graphene based materials, Biosensor Bioelectronics Oct. 15, 2020).

WO 2012/047865 A2 discloses a method where M13 bacteriophage was grafted into an array of poly (3,4-ethylenedioxythiophene) (PEDOT) nanowire generated hybrids conducting polymers and replicable genetic packages (rgps) such as viruses. The incorporation of rgps into the polymeric backbone of PEDOT occurs during electro-polymerization via lithographically patterned nanowire electrodeposition (LPNE). The resultant arrays of rgps-PEDOT nanowires enable real-time, reagent-free electrochemical biosensing of analytes in physiologically relevant buffers.

In another disclosure, U.S. Pat. No. 8,859,297, a detection system utilizing a two-particle detection system includes immuno-functionalized conductive polymer nanoparticles as labels and immuno-functionalized magnetic nanoparticles as separators/concentrators for a particular target analyte. The conductive polymer portion of the analyte conjugate is electrically activated to form an electrically activated analyte conjugate having an increased electrical conductivity relative to the analyte conjugate as originally formed. The electrically activated analyte conjugate can then be detected by any suitable means, such as by conductimetric or electrochemical detection.

U.S. Patent Application Publication No. 2017/0227486 discloses materials and methods of fabricating and using an electrochemical biosensor for continuous detection of biological analytes. In the specific disclosure, the biosensor detects a given analyte when the analyte binds with a molecularly imprinted polymer (MIP) matrix immobilized atop a sensing substrate eliminating the need for a redox probing agent commonly found in electro chemical biosensors. Furthermore, the detection sensitivity of the biosensor is enhanced by modifying the electrode surface with a plurality of nanoscopic metallic structures.

U.S. Patent Application Publication No. 2022/0018797 features a sensor for detecting a virus with a sensor tip. The sensor tip includes a working electrode that includes a conductive material that is resistant to corrosion, a support, and a catalyst. The sensor tip also includes a counter electrode with an electrocatalyst. The counter electrode is operably connected to the working electrode. The sensor tip allows for the change in current to be detected when the sensor tip is inserted into a sample, through the use of the working electrode and the counter electrode. By detecting the change in current, the sensor tip is able to detect the virus. This is a method for detecting a virus with a sensor tip inserting the sensor tip into the collected air sample impinged with the electrolyte solution.

Michal Oteypka et al summarize in their review, [10.1016/j.bios.2020.112436] the current state-of-the-art applications of graphene-based systems for sensing a variety of viruses, e.g., SARS-CoV-2, influenza, dengue fever, hepatitis C virus, HIV, rotavirus and Zika virus. General principles, mechanisms of action, advantages and drawbacks are presented to provide useful information for the further development and construction of advanced virus biosensors. The unique and tunable physicochemical properties of graphene-based nanomaterials make them ideal candidates for engineering and miniaturization of biosensors.

The above techniques mostly rely on the change in the transport properties such as DC and AC conductivity after exposure to viral particles due to n-type doping of the alkaline ions on the spike proteins of the virus. These techniques, however, are believed to have substantial limitations that inhibit their application in preparing reliable and effective biosensors towards the detection of aerosolized virus particles. Such limitations are believed to be due to factors such as: a) significant variation in the sensor quality and hence transport properties of the bio-sensor over batches b) influence of environmental conditions such as temperature, humidity etc. on the conductivity of π-electrons; and c) variation in the binding of the viral particles with the conducting polymers due to relatively large dimension of the conducting strip leading to a lower signal to noise ratio creates a localized in the impedance instead of uniform bulk change that is observed in liquid media as disclosed in U.S. patent Ser. No. 17/537,979, titled Systems and Processes for Detecting Aerosolized Viral Load, which discloses the use of engineered liquid media. Compared to uniform bulk changes in impedance observed in liquid media, as disclosed in U.S. patent Ser. No. 17/537,979, titled Systems and Processes for Detecting Aerosolized Viral Load, the conductivity in solid state media is governed by the mobility and density of charge carriers (electrons/holes/polarons/bi-polarons), and these parameters are dependent on not only the type of virus but also on the substrate temperature, characteristics of the electrodes, incident velocity of the viral particles falling on the solid substrate, and the dispersion of the virus particles on the substrate surface as well as its crystallization. Thus, generating a repeatable and reliable shift in the transport properties due to virus-induced doping in the solid substrate is difficult and not repeatable, and hence the resulting signal cannot be commercially used for reliable and consistent detection of viral particles.

SUMMARY

In one aspect of the disclosed technology, a system for detecting aerosolized virus particles includes an air sampler, temperature-controlled π-bonded solid-state sensors of different shapes and dimensions either in the form of straight line or made in zigzag/helical arrangement and two/four/eight electrodes associated with each of the solid-state sensor. The air sampler is configured to blow an air sample that may contain viral particles onto the 7E-bonded solid-state sensors, which are maintained at different relative temperatures. The subsequent interaction of virus particles with the conducting polymer then results in a change in the transport properties of the sensor that can be traced using electrical characterization through the electrodes that facilitate the calculation of the V (voltage) vs. I (current) characteristics of the solid-state strips at the different temperatures, which in turn can indicate the presence or absence of virus particles, and the type of virus more specifically.

In another aspect of the disclosed technology, the system flexibly can be configured to determine the following parameters:

A. The relative change in the bandgap after exposure to the viral particles, using standard current-voltage characteristics at different temperatures.

B. Measurement of chemiresistance through frequency measurement using a resistance-capacitance (RC) timer circuit; and the relative change in the frequency characteristics after exposure to the viral particles; and C. The shift of the AC impedance after virus exposure from a reference value measured through impedance spectroscopy.

In another aspect of the disclosed technology, the system combines and processes the data and features from the above parameters A, B, and C to provide a biosensor that can reliably detect the presence of the airborne viruses.

In another aspect of the disclosed technology, the use of parameter A (shift in bandgap property) makes it possible to isolate and identify specific types of viruses as well, since each virus will create specific band-gap characteristics with a specific $\pi$-bonded solid-state material.

In another aspect of the disclosed technology, a system for detecting aerosolized viral loads includes one or more pi-conjugated solid-state sensors; a plurality of electrodes in electrical contact with the one or more one pi-bonded solid-state sensors; an air sampler configured to direct air samples onto the one or more pi-bonded solid-state strips at the approximate locations of the plurality of electrodes; and one or more temperature-regulating devices configured to maintain the one or more pi-bonded solid-state sensors at different temperatures.

The system further includes a computing device communicatively coupled to the plurality of electrodes and configured to determine a presence, absence, and/or type of viral particles on the one or more pi-bonded solid-state sensors based on one or more of: a shift in the bandgap property of the one or more pi-bonded solid-state sensors determined from voltage vs. current characteristics of the one or more pi-bonded solid-state sensors at the different temperatures; resistance-capacitance characteristics of the plurality of electrodes based on a frequency response of the one or more one pi-bonded solid-state sensors to the applied voltage, and a change in the frequency characteristics due to the presence of the viral particles; and a shift in conductance of the one or more one pi-bonded solid-state sensors due to the presence of the viral particles.

In another aspect of the disclosed technology, a substrate of the sensors comprises natural products which act as a base material for the sensors.

In another aspect of the disclosed technology, the natural products comprise cellulose and proteins.

In another aspect of the disclosed technology, the natural products comprise at least one of paper, wool, cotton, and silk.

In another aspect of the disclosed technology, the base materials are coated with a pi-conjugated material.

In another aspect of the disclosed technology, the pi-conjugated material is made of at least one of a conducting polymer such as polyaniline, polypyrrole, poly(3,4-ethyl-enedioxythiophene), poly(3,4-ethylenedioxythiophene)-polystyrene sulphonate, polyacetylene, poly(3,4-ethylenedi-oxythiophene), poly(p-phenylene vinylene) and polythiophene or graphene/graphene like materials such as RGO, GO, C60, CNT, CQD.

In another aspect of the disclosed technology, a dimension of the sensor is 1D/2D/3D or a combination of two or more of same or different kind.

In another aspect of the disclosed technology, each of the one or more pi-conjugated solid-state sensors comprises a substrate, and an electrically-conductive film disposed on the substrate.

In another aspect of the disclosed technology, the electrically-conductive film comprises at least one of polyaniline, polypyrrole, poly(3,4-ethylenedioxythiophene), poly(3,4-ethylenedioxythiophene)-polystyrene sulphonate, polyacetylene, poly(3,4-ethylenedioxythiophene), poly(p-phenylene vinylene) and polythiophene or graphene/graphene like materials.

In another aspect of the disclosed technology, the system further includes an air stream divider in fluid communication with the air sampler and configured to divide a primary airstream exiting the air sampler into three or more secondary airstreams.

In another aspect of the disclosed technology, the plurality of electrodes are configured to apply voltages to the one or more one pi-bonded solid-state sensors; and to sense currents in the one or more one pi-bonded solid-state sensors in response to the applied voltages.

In another aspect of the disclosed technology, the electrodes are configured to feed current to the one or more pi-bonded solid-state sensors, and to pick up a resulting voltage from the one or more pi-bonded solid-state sensors.

In another aspect of the disclosed technology, the system includes not more than one of the pi-conjugated solid-state sensors.

In another aspect of the disclosed technology, the substrate includes at least one of natural cellulose and a protein.

DESCRIPTION OF THE DRAWINGS

The accompanying drawings, which are incorporated herein and constitute part of this specification, are illustrative of particular embodiments of the present disclosure and do not limit the scope of the present disclosure. The drawings are not to scale and are intended for use in conjunction with the explanations in the following detailed description.

FIG. 1 is a diagrammatic illustration of a system for detecting aerosolized viral particles.

FIG. 2 is a diagrammatic illustration of another system for detecting aerosolized viral particles.

FIG. 3 is a schematic illustration of a subsystem for capturing and processing analog voltage data generated by the systems shown in FIGS. 1 and 2.

DETAILED DESCRIPTION

The following discussion omits or only briefly describes conventional features of the disclosed technology that are apparent to those skilled in the art. It is noted that various embodiments are described in detail with reference to the drawings, in which like reference numerals represent like parts and assemblies throughout the several views. Reference to various embodiments does not limit the scope of the claims appended hereto. Additionally, any examples set forth in this specification are intended to be non-limiting and merely set forth some of the many possible embodiments for the appended claims. Further, particular features described herein can be used in combination with other described features in each of the various possible combinations and permutations.

Two exemplary embodiments of systems for detecting aerosolized viral particles are described herein: a system 1, shown in FIG. 1, and a system 2, shown in FIG. 2.

System 1

The system 1 includes a divided air sampler 12 configured to have a pointed viral drop, and co-located voltage pickups, for relatively sensitive applications.

1A The system 1 comprises 4 major components: a) an air sampler 12 that drives a primary airstream from the ambient environment; b) an air stream divider 14 that divides the primary airstream into three or more secondary airstreams using a lumen structure; c) sensors 16 of dimension such as 1D/2D/3D made on substrates 18 like natural cellulose and proteins (e.g., paper, wool, cotton, silk etc.) that are electrically conductive due to presence of a film 19 of conducting polymers polyaniline, polypyrrole, poly(3,4-ethylenedioxythiophene), poly(3,4-ethylenedioxythiophene)-polystyrene sulphonate, polyacetylene, poly(3,4-ethylenedioxythiophene), poly(p-phenylene vinylene) and polythiophene or graphene/graphene like materials such as RGO, GO, C60, CNT, CQD), and onto which the secondary airstreams fall; and d) a Peltier thermal cooler 20 inside of which the entire system 1 is housed so that the substrate strips 18 can be maintained at different desired temperatures, with the different temperatures T1, T2, T3, etc. being achieved and maintained using small local heating systems 22.

2A Each substrate strip 18 is provided, or hooked with a four-probe arrangement comprising two electrodes 24 to feed current, and two electrodes 26 to pick up the resulting voltage, so that the surface conductivity of the substrate 18 can be measured locally from the locations of virus interaction, and contributions from other contact resistances can be eliminated. This gives I-V characteristics for each substrate strip 18 at its respective temperature, from which the shift in the bandgap, and the shift in the conductance from a reference conductance, can be determined. Thus, this measurement provides a determination of the above-noted parameters A and C. This arrangement provides more control over the ability to locally measure conductivity only at the location on the substrate strip 18 at which virus particles have fallen.

3A Each substrate strip 18 also forms part of an RC circuit that, along with the four probes 24, 26 associated with the strip 18, measures the change in the RC value through frequency measurement which, along with statistical/signal features extracted from the resulting signal, is used to determine the virus vs. no-virus signature, i.e., whether the characteristics of the signal indicate the presence or absence of virus particles on the substrate 18. This provides the basis for the determination of above-noted parameter B.

In the configuration of system 1, the voltage pickup, i.e., measurement, will be from the place where virus particles have fallen concentratedly, thereby increasing the sensitivity and homogeneity of the effect of the virus induced doping of the substrate 18.

System 2

System 2, shown in FIG. 2, uses a multiple voltage drop pick up 42 and a single strip sensing element 40, for a less complicated configuration relation to system 1.

1B System 2 comprises: a) air-sampler 30 that drives, i.e., samples, an air sample from the ambient environment; b) sensors 32 of dimension such as 1D/2D/3D made on substrates 34 like natural cellulose and proteins (e.g., paper, wool, cotton, silk etc.) that are electrically conductive due to presence of a film 36 of conducting polymers such as polyaniline, polypyrrole, poly(3,4-ethylenedioxythiophene), poly(3,4-ethylenedioxythiophene)-polystyrene sulphonate, polyacetylene, poly(3,4-ethylenedioxythiophene), poly (p-phenylene vinylene) and polythiophene or graphene/graphene like materials such as RGO, GO, C60, CNT, CQD, and onto which the secondary airstreams fall; and c) a Peltier element 38 under which the entire strip 40 is positioned and which provides a steady constant temperature gradient on the solid strip 40.

2B The strip 40 has minimum of three, and preferably four, voltage pickups 42 positioned at different locations along the strip 40. Thus, multiple "V vs. I" curves can be obtained, each at a different temperature. This provides the basic data to determine the above-noted parameters A and C.

3B The substrate 34 also is part of the RC circuits that measure the increase or decrease of RC value via frequency measurement and which, along with the statistical/signal features extracted from the signal, are used to determine the virus vs. no-virus signature. This provides the basis for the determination of the above-noted parameter B.

In both system 1 and system 2, a constant current is applied through the substrates 18, 34 using the current sourcing probes. Referring to FIG. 3, a 24-bit Sigma-Delta ADC samples the voltage at voltage-pick up probes 42 at 100 ksps and send it to a powerful MPU to analyze the data. High sampling rate and resolution are desirable, to help to understand the characteristics of the voltage during the viral load exposure. Small changes in the amplitude of the voltage with time can be captured very efficiently using this scheme as shown in FIG. 3.

Systems 1 and 2 both can be edge-cloud enabled for IoT compliant applications (such as sending alerts etc.) as described in co-pending U.S. patent application Ser. No. 17/537,979.

Measurement of Parameters a, B, C

As noted above, the system 1 and the system 2 have the flexibility to be configured to generate the following parameters:

A. The relative change in the bandgap after exposure to the viral particles, using standard current-voltage characteristics at different temperatures.

B. Measurement of chemiresistance through frequency measurement using a resistance-capacitance (RC) timer circuit; and the relative change in the frequency characteristics after exposure to the viral particles; and C. The shift of the AC impedance after virus exposure from a reference value measured through impedance spectroscopy.

A. As is well known, the relationship between current (I), bandgap (Eg) and absolute temperature T (in Kelvin) is given by following equation (where k=Boltzmann constant):

$$I = I_0 e^{-\left(\frac{Eg}{kT}\right)}$$

Thus, for a long time, scientists have estimated the bandgap of a system from the slope of Log(I) and 1/T characteristics.

Since viral particles act as n-type dopants to $\pi$-electron conducting solids like conducting polymers or graphene, attachment of viral particles to the surface alters its chemiresistive properties, which in turn results in a change in the bandgap of the material. From the measured current-voltage characteristics, the log of current (I) obtained from the multiple (e.g., four) conductive strips kept at temperatures T1, T2, T3, T4, etc., can provide an estimate to the bandgap by a simple linear fitting. Due to the nature of a logarithm and finding only the slope, this measurement will be substantially free from the effects of a) non-uniformity of electrodes; and b) dispersive and dimensional issues relating to the strip size in relation to the dimensions of the viral particles.

B. Looking at the RC (resistor-capacitance) characteristic of the biosensor using a frequency measurement and finding the relative change in frequency characteristics as viral particles are falling on the substrate, a machine learning based method as described in U.S. patent Ser. No. 17/537,979, the contents of which are incorporated by refence herein in their entirety, is used to separate the signal artifacts that are resulting from the virus vs no virus situation. The signal artifacts can be, for example, standard deviation, co-efficient of variation, etc.

C. Also, the relative shift in the impedance of the sensor before and after exposure to the virus particles can be used to detect the presence of virus particles and thereby reduce the occurrence of false positive and false negative results. This impedance-based measurement technique mostly analyzes the influence of viral particles on the transport properties of the biosensors and is a promising route to detect virus particles in solid state media owing to its high sensitivity, precision, and nondestructive nature. Impedance, like conventional resistance, is the total electron opposition within a circuit and often is presented as a complex number that considers contributions from resistors, capacitors, and inductors. Thus, when the response of the present sensor system was recorded using low amplitude alternating current (AC) voltages over a range of frequencies, the potential (E) can be expressed following AC analogue of Ohm's law as $E=I*Z$, where, I is the current through the system having an impedance of Z.

In the Cartesian form of complex impedance Z, resistance (R) is the real component, whereas reactance (X) is the imaginary portion which is determined by considering the contribution of inductance and capacitance. Therefore, expressing impedance as a complex number designates resistance as the real component and the sum of capacitance and inductance as the imaginary component or reactance as $Z=R+jX$, and hence the absolute magnitude of the impedance component can therefore be given using the quadratic formula $Z=\sqrt{(R^2+X^2)}$.

Thus, the impedance characteristics include both the resistive and capacitive components of the virus response on the biosensors (considering the contribution from inductance to be insignificant) and, therefore, the change in the impedance before and after exposure to virus particles is more profound than just the change in the resistive measurement. Moreover, the time dependent response of the impedance amplitude can also reveal how electrons interact with the electrode surface, as well as information about the ion size, and hence the type of the virus (see Y. Barsukov, &. J. Macdonald, "Impedance Spectroscopy: Theory, Experiment, and Applications, Edition 2", 2005, Wiley-Interscience, (ISBN: 9780471716242).

The above determinations of parameters A, B, and C can be made by a suitable computing device, programmed with computer-executable instructions that, when executed by the computing device, cause the computing device to carry out the logical operations in accordance with the above-noted formulae and techniques. The computing device can include, for example, a processor, such as a microprocessor; an internal bus; a memory communicatively coupled to the processor via the bus; computer-executable instructions stored in the memory; and an input-output interface communicatively coupled to the internal bus. The processor, upon executing the computer-executable instructions, is configured to carry out the logical operations in accordance with the above-noted formulae and techniques. The computing device can have other configurations in alternative embodiments.

We claim:

1. A system for detecting aerosolized viral loads, comprising:
   one or more pi-conjugated solid-state sensors;
   a plurality of electrodes in electrical contact with the one or more one pi-bonded solid-state sensors;
   an air sampler configured to direct air samples onto the one or more pi-bonded solid-state strips at the approximate locations of the plurality of electrodes;
   one or more temperature-regulating devices configured to maintain the one or more pi-bonded solid-state sensors at different temperatures; and
   a computing device communicatively coupled to the plurality of electrodes and configured to determine a presence, absence, and/or type of viral particles on the one or more pi-bonded solid-state sensors based on one or more of: a shift in the bandgap property of the one or more pi-bonded solid-state sensors determined from voltage vs. current characteristics of the one or more pi-bonded solid-state sensors at the different temperatures; resistance-capacitance characteristics of the plurality of electrodes based on a frequency response of the one or more one pi-bonded solid-state sensors to the applied voltage, and a change in the frequency characteristics due to the presence of the viral particles; and a shift in conductance of the one or more one pi-bonded solid-state sensors due to the presence of the viral particles.

2. The system of claim 1, wherein a substrate of the sensors comprises natural products which act as a base material for the sensors.

3. The system of claim 2, wherein the natural products comprise cellulose and proteins.

4. The system of claim 3, wherein the natural products comprise at least one of paper, wool, cotton, and silk.

5. The system of claim 2, wherein the base materials are coated with a pi-conjugated material.

6. The system of claim 5, wherein the pi-conjugated material is made of at least one of a conducting polymer such as polyaniline, polypyrrole, poly(3,4-ethylenedioxythiophene), poly(3,4-ethylenedioxythiophene)-polystyrene sulphonate, polyacetylene, poly(3,4-ethylenedioxythiophene), poly(p-phenylene vinylene) and polythiophene or graphene, RGO, GO, C60, CNT, or CQD.

7. The system of claim 1, wherein the sensor is one or more 1D sensors, one or more 2D sensors, one or more 3D sensors, or a combination of 1D, 2D, and/or 3D sensors.

8. The system of claim 1, wherein each of the one or more pi-conjugated solid-state sensors comprises a substrate, and an electrically-conductive film disposed on the substrate.

9. The system of claim 8, wherein the substrate comprises at least one of natural cellulose and a protein.

10. The system of claim 8, wherein the electrically-conductive film comprises at least one of polyaniline, polypyrrole, poly(3,4-ethylenedioxythiophene), poly(3,4-ethylenedioxythiophene)-polystyrene sulphonate, polyacetylene, poly(3,4-ethylenedioxythiophene), poly(p-phenylene vinylene) and polythiophene or graphene.

11. The system of claim 1, further comprising an air stream divider in fluid communication with the air sampler and configured to divide a primary airstream exiting the air sampler into three or more secondary airstreams.

12. The system of claim 1, wherein the plurality of electrodes are configured to apply voltages to the one or more one pi-bonded solid-state sensors; and to sense currents in the one or more one pi-bonded solid-state sensors in response to the applied voltages.

13. The system of claim 1, wherein the electrodes are configured to feed current to the one or more pi-bonded solid-state sensors, and to pick up a resulting voltage from the one or more pi-bonded solid-state sensors.

* * * * *